United States Patent
Mokete (10) Patent No.: US 12,370,065 B2
(45) Date of Patent: Jul. 29, 2025

(54) IMPLANTABLE ELECTRONIC DEVICE AND ENDOPROSTHESIS

(71) Applicant: Lipalo Mokete, Bryanston (ZA)

(72) Inventor: Lipalo Mokete, Bryanston (ZA)

( * ) Notice: Subject to any disclaimer, the term of this patent is extended or adjusted under 35 U.S.C. 154(b) by 799 days.

(21) Appl. No.: 17/408,198

(22) Filed: Aug. 20, 2021

(65) Prior Publication Data

US 2021/0378841 A1    Dec. 9, 2021

Related U.S. Application Data (63) Continuation-in-part of application No. PCT/IB2020/050729, filed on Jan. 30, 2020.

(30) Foreign Application Priority Data

Feb. 22, 2019    (ZA) .................................. 2018/05590

(51) Int. Cl.
    *A61F 2/46*      (2006.01)
    *A61F 2/30*      (2006.01)
    *A61F 2/38*      (2006.01)

(52) U.S. Cl.
    CPC .......... *A61F 2/468* (2013.01); *A61F 2/30771* (2013.01); *A61F 2/3859* (2013.01); *A61F 2/389* (2013.01)

(58) Field of Classification Search
    CPC .... A61F 2/468; A61F 2/30771; A61F 2/3859; A61F 2/389; A61F 2/38; A61B 5/4528; A61B 5/4851; A61B 2562/0219
See application file for complete search history.

(56) References Cited

U.S. PATENT DOCUMENTS

| 7,195,645 | B2 * | 3/2007 | Disilvestro | ............ | A61B 5/076 600/587 |
| 2014/0275815 | A1 | 9/2014 | Stein et al. | | |
| 2019/0239804 | A1 * | 8/2019 | Vena | ...................... | A61B 5/686 |

FOREIGN PATENT DOCUMENTS

| WO | 2014209916 A1 | 12/2014 |
| WO | 2015196131 A1 | 12/2015 |

OTHER PUBLICATIONS

International Search Report issued in International Application No. PCT/IB2020/050729 dated Jul. 8, 2020 (4 pages).

(Continued)

*Primary Examiner* — Jerrah Edwards
*Assistant Examiner* — Jose H. Trevino, III
(74) *Attorney, Agent, or Firm* — OSHA BERGMAN WATANABE & BURTON LLP (57) ABSTRACT

An implantable electronic device (12) and an endoprosthesis activity monitoring system (10) with a knee prosthesis (11) are developed. Knee prosthesis (11) has at least two blind cavities (35.1, 35.2), one in a lateral aspect of a femoral component (11.1) or tibial component (11.2), within which devices (12) are removably mounted and remote device (18) in wireless communication with devices (12) to receive data transmitted from it. Devices (12) are configured to track movement of the prosthesis (11) and to report same to the remote device (18). Devices (12) are self-contained and include an accelerometer (13), memory (15), a wireless communication module (14), processor (17) and a battery (16). Activity information analysed allows for early diagnosis of implant specific problems like loosening of the prosthesis. Location of devices (12) in the lateral aspects improves accessibility. Devices can be removed by minor surgery without compromising structural integrity of the knee prosthesis.

13 Claims, 4 Drawing Sheets

(56) References Cited

OTHER PUBLICATIONS

Written Opinion issued in International Application No. PCT/IB2020/050729 dated Jul. 8, 2020 (5 pages).

* cited by examiner

IMPLANTABLE ELECTRONIC DEVICE AND ENDOPROSTHESIS

FIELD OF INVENTION

The invention relates generally to medical prosthetics and more specifically to an endoprosthesis fitted with an implantable electronic device for measuring activity of the endoprosthesis.

BACKGROUND OF INVENTION

Contemporary knee replacements were developed in the early 1970s and since then refinements in the surgical technique and improvements in the design and materials of the prosthesis have contributed to the knee currently being the most replaced joint in the body. As the outcomes and longevity of implanted knee prosthesis improved, orthopaedic surgeons recognized the importance of assessing and documenting performance of the implant.

A Dr. Insall and his colleagues at the North American Knee Society developed a knee scoring system to assess the performance of the knee following knee replacement surgery. They published a Knee Society Score (KSS) in 1989 based on set criteria and made the score available for use by orthopaedic surgeons worldwide. However, reliability, responsiveness and validity of the scoring system was found to be lacking over time primarily because of deficiencies in Patient Reported Outcome Measures (PROMs). The KSS was subsequently updated in 2011 to include a more extensive section on PROMs and it is still widely used to reflect performance of knee replacements. Other PROMs in common use include Western Ontario MacMaster University Osteoarthritis Index (WOMAC) and the Oxford Knee Score.

Over the years, innovations in prosthetic design, implant materials and implantation techniques have resulted in better functioning of knee prosthesis and patient satisfaction rates have improved as a consequence. There is now greater emphasis on improvement of function following knee replacement surgery and the aim of the surgery has evolved to restoring quality of life.

Over the last decade, there has been greater demand by healthcare executives and funders for the Orthopaedic community to demonstrate the effectiveness of total knee replacement. Traditional outcome measures that were in common use before like the Knee Society Score are too subjective and insensitive hence, the development of specific outcome measures that are focused on the patient experience. The perspective of the recipient of the total knee replacement and fulfillment of his or her expectations post-operatively is now recognized as an important outcome measure. It is generally accepted that Patient Reported Outcome Measures (PROMs) are the most objective instruments available to us to date to assess outcomes following joint replacement surgery. PROMs are administered in the form of self-reported questionnaires. Commonly used PROMs include The New Knee Society Score, WOMAC and Oxford Knee Score. However, there are many limitations to PROMs and currently there is no single validated, reliable and responsive PROM to assess all aspects of total knee replacement surgery.

A return to previous activity levels is the ultimate goal of knee replacement surgery and an important component of outcome of the intervention. Low activity levels and specifically long periods of sedentary behavior are hazardous to general health. On the other hand, extremely high activity levels have been associated with early failure of the knee replacement. Hence, the aim should be for a more balanced activity profile following knee replacement surgery. Assessment of quantity of activity is currently done using crude instruments in the form of patient questionnaires, examples being the Lower Extremity Activity Score (LEAS) and the UCLA Activity score. There is a need for a more sensitive and accurate measure of the quantity of activity. Commercially available activity trackers have the potential for short-term activity assessment following knee replacement surgery. However, they are limited in conveying critical information on medium to long-term activity profiles.

PROMs are largely based on level of function, pain, quality of life and satisfaction. The scoring of PROMs is susceptible to a patient's subjectivity and is dependent upon a number of parameters including the patient's mental status, hospital experience, cultural background, socioeconomic status and body mass index. Patient bias and ability to recall events also affects PROMs. Other limitations include a floor/ceiling effect and lack of responsiveness.

Accelerometers are electromechanical devices or motion sensors that are used to measure proper acceleration. Proper acceleration is the acceleration of a body relative to a free-fall, or inertial, observer who is momentarily at rest relative to the body being measured. Accelerometry, which, is the science of quantifying movement through the use of accelerometers offers one the ability to give objective accurate information on the quantity of limb movement over a defined period. Accelerometers are commonly used in the healthcare space in the form of electronic devices that can be worn on the body. These are commonly referred to as wearables with one of the most popular applications being activity tracking. The devices are able to relay information regarding vital body functions including the pulse and parameters such as the number of steps taken, and distance travelled. Sophisticated activity trackers are also able to quantify activity. They can accurately distinguish sedentary behavior from light physical activity and vigorous activity.

There is evidence to show that excessive periods of sedentary behaviour is detrimental to one's health. Advanced degenerative disease of the knee reduces the quantity of activity and can potentially result in an increase in sedentary activity. Wearables are useful for the purposes of quantifying activity in patients following knee replacement surgery and alerting the healthcare worker of unhealthy patterns of physical behavior. The accuracy of quantifying movement improves the closer the measuring device or activity monitor is to the limb under assessment and long-term movement patterns in the order of weeks to months offer more useful information on activity than short-term quantification. Wearables worn on the thigh tend to be uncomfortable and can be a source of irritation making compliance a challenge and long-term wear impractical.

The present invention aims, at least to some extent, to alleviate the drawbacks discussed above.

SUMMARY OF INVENTION

In accordance with the invention, there is provided an implantable electronic device which includes:
   an electromechanical motion sensor which is configured to measure acceleration and rotation of the implantable electronic device;
   memory coupled to the electromechanical motion sensor; the memory being configured to store data measured by the electromechanical motion sensor;

a wireless communication module which is communicatively linked to the electromechanical motion sensor and/or memory and is configured to communicate with a remote device; and a power source configured to power the wireless communication module;

wherein the implantable electronic device is in the form of a self-contained, one-piece, integrated form factor and further includes a casing which defines an inner cavity, the casing being configured to house the electromechanical motion sensor, memory, wireless communication module and power source in the inner cavity such that the implantable electronic device, as a whole, is configured to be removably mounted to a lateral aspect of a femoral or tibial condyle of a knee prosthesis in an area of a knee which has least soft tissue cover which renders the electronic device easily removable, serviceable and/or replaceable by way of only minor surgery without compromising structural integrity of the knee prosthesis.

The casing may include two complementary parts which are operatively disconnectably coupled together to form a serviceable pod. The two complementary parts may comprise male and female parts which mate in snap fit or interference fit fashion. The casing may be squat. The two complementary parts may comprise a cover and a base.

The casing may be manufactured from cobalt chrome molybdenum alloy, titanium, titanium alloy or any other suitable material compatible with material properties of the knee prosthesis.

The implantable electronic device may be configured to be mounted in a blind cavity formed in the lateral aspect of the femoral or tibial condyle of the knee prosthesis. The blind cavity may have dimensions of 20 mm in length, 15 mm depth, and 3.5 mm breadth. Preferably, the blind cavity may have dimensions of 15 mm in length, 15 mm depth and 3.5 mm breadth. The dimensions of the blind cavity are not limited to the above and may vary according to specific design requirements or specifications.

The electromechanical motion sensor may be an accelerometer. The accelerometer may be a multi-axis accelerometer. The accelerometer may be a three-axis piezoelectric accelerometer.

The power source may include a battery which is configured to power the electromechanical motion sensor and the wireless communication module. The battery may have a lifespan of at least 5 years. The battery may be rechargeable battery. The battery may be configured to be received in the blind cavity.

The power source may include an inductive charger which includes a receiving circuit coupled to the battery. The receiving circuit may be coupled to the electromechanical motion sensor and the wireless communication module. The inductive charger may further include an inductive charging circuit which is operatively not mounted to the implantable electronic device, nor to the knee prosthesis but is configured inductively to power the receiving circuit.

The implantable electronic device may include a processor which is coupled to the electromechanical motion sensor, memory and the wireless communication module. The implantable electronic device may include first and second electromechanical motion sensors. The first electromechanical motion sensor is configured to be accommodated in a blind cavity formed in the lateral aspect of the femoral condyle of the knee prosthesis. The second electromechanical motion sensor is configured to be received in a second blind cavity formed in a lateral aspect of the tibial condyle of the knee prosthesis.

In accordance with another aspect of the invention, there is provided an endoprosthesis which is configured to be fitted to a subject as a replacement body part, the endoprosthesis having a first part articulating with a second part and a first implantable electronic device as described above removably installed in a blind cavity defined in either one of the first part or second part. At least two implantable electronic devices as described above may be installed in two separate blind cavities, one defined in the first part and the other in the second part.

The endoprosthesis may be a knee prosthesis. The first part may be a femoral component and the second part may be a tibial component of the knee prosthesis. The blind cavity may be formed in a lateral aspect of a femoral condyle of the femoral component of the knee prosthesis. The blind cavity may have dimensions of 20 mm in length, 15 mm depth, and 3.5 mm breadth. The blind cavity may be configured removably to receive the first implantable electronic device therein thus allowing for easy access to the first implantable electronic device by way of only minor surgery to remove/replace the first implantable electronic device, if need be.

Another or second blind cavity may be formed in a lateral aspect of a tibial condyle of the tibial component of the knee prosthesis. This second blind cavity may have dimensions of 20 mm in length, 15 mm depth, and 3.5 mm breadth. A second implantable electronic device as described above may be removably received in the second blind cavity.

The endoprosthesis may include at least one cover which is configured removably to be secured over one of the blind cavities thus retaining the first or second implantable electronic device in the blind cavity.

The invention extends to an endoprosthesis activity monitoring system which includes:

an endoprosthesis as described above fitted to, or mountable to a subject; and a remote device which is communicatively coupled to the wireless communication module of the first and/or second implantable electronic device and is configured:

wirelessly to interrogate the first and/or second implantable electronic device to obtain data measured by the electromechanical motion sensor;

to process the obtained data to determine an activity level and/or condition of the endoprosthesis; and to report processed information to a user.

The endoprosthesis activity monitoring system may be configured to determine relative acceleration, rotation, or tilt of the first and second implantable electronic devices received in the separate blind cavities in the first and second parts of the endoprosthesis, respectively.

BRIEF DESCRIPTION OF DRAWINGS

The invention will now be further described, by way of example, with reference to the accompanying drawings.

In the drawings.

DETAILED DESCRIPTION

The following description of the invention is provided as an enabling teaching of the invention. Those skilled in the relevant art will recognise that many changes can be made to the embodiments described, while still attaining the beneficial results of the present invention. It will also be apparent that some of the desired benefits of the present invention can be attained by selecting some of the features of the present invention without utilising other features. Accordingly, those skilled in the art will recognise that modifications and adaptations to the present invention are possible and can even be desirable in certain circumstances, and are a part of the present invention. Thus, the following description is provided as illustrative of the principles of the present invention and not a limitation thereof.

Figure 1:
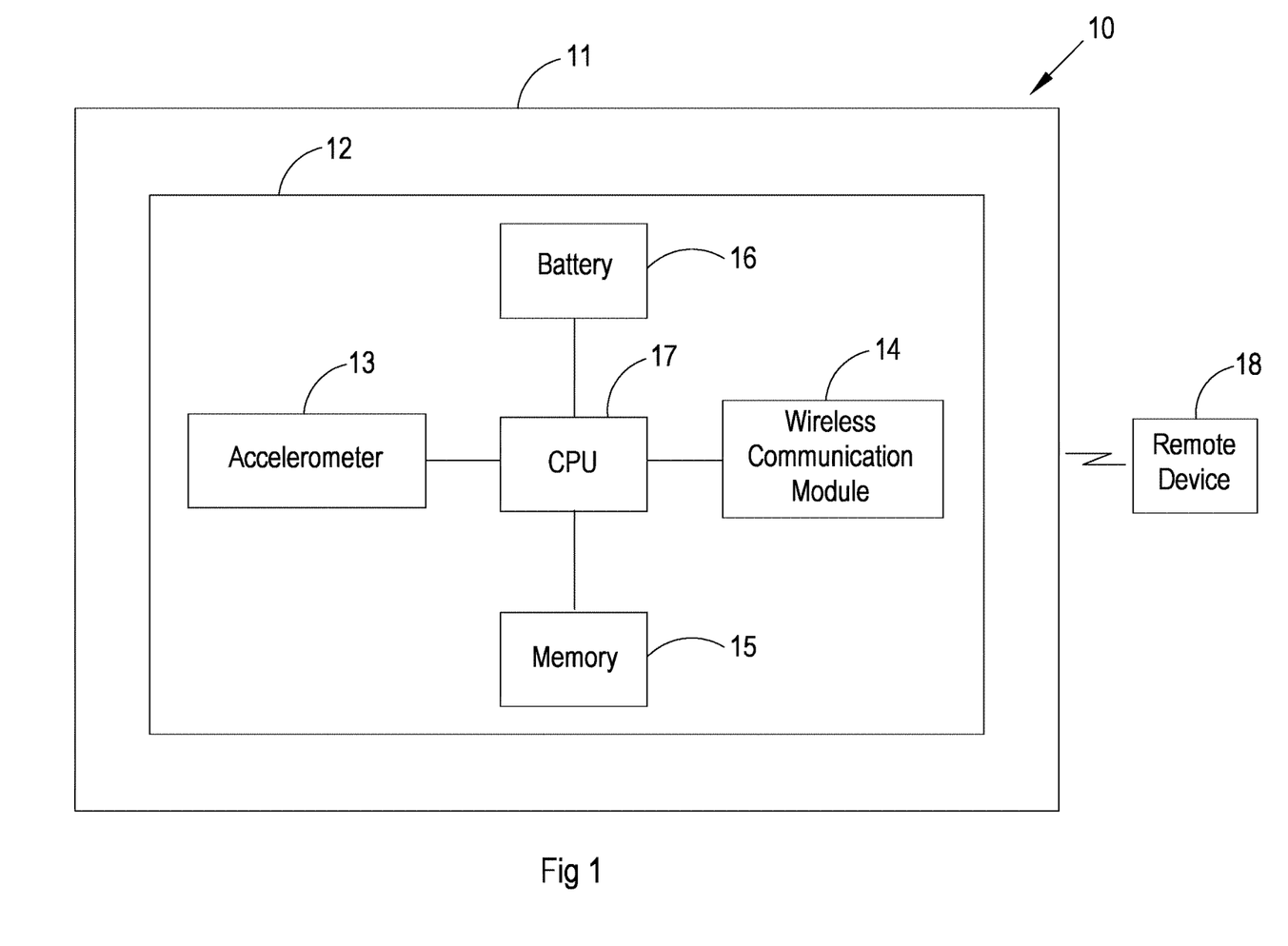
FIG. 1 shows a functional block diagram of an endoprosthesis activity monitoring system in accordance with a first aspect of the invention, which system includes an implantable electronic device in accordance with a second aspect of the invention.
Figure 4A:
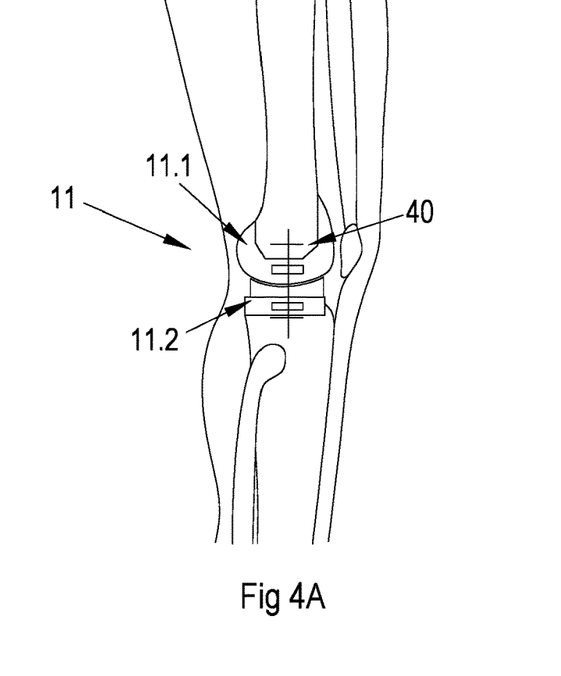
FIGS. 4A and 4B show side elevations of the endoprosthesis of FIG. 3 fitted to a patient.

In FIG. 1 reference numeral 10 refers generally to an endoprosthesis activity monitoring system in accordance with the invention. The system 10 includes an endoprosthesis 11, which in this example embodiment is in the form of a knee prosthesis configured to be fitted as a replacement body part to a subject or patient (see FIGS. 4A and 4B). The knee prosthesis illustrated in this example happens to be a complete knee prosthesis. It is envisaged that the invention may also find application in partial knee prosthesis. In this example embodiment, the endoprosthesis activity monitoring system 10 includes at least two implantable electronic devices 12.1, 12.2 (although only one implantable electronic device 12 has been illustrated in FIG. 1) which are operatively mounted to or received within separate cavities 35.1, 35.2 provided in the endoprosthesis 11, as will be explained in more detail below. The system 10 also includes an external remote device 18 which is configured wirelessly to interrogate the implantable electronic devices 12 in order to glean recordings or measurements from them. To this end, each implantable electronic device 12 includes a processor or CPU 17 and a wireless communication module 14 which is communicatively linked to the processor 17 and is configured to communicate with the remote device 18 using any suitable wireless communication protocol. The wireless communication module 14 may be laterally disposed within the cavity to ensure least possible interference between the wireless communication module 14 and the remote device 18. Each implantable electronic device 12 also includes at least one accelerometer 13 which is configured to measure acceleration and rotation of at least part of the endoprosthesis 11. The accelerometer 13 may be a three-axis piezoelectric MEMS accelerometer. The implantable electronic device 12 also includes memory 15 for storing recorded measurements, data or readings of the accelerometer 13 and a power source in the form of a battery 16. The battery 16 may be a rechargeable battery. The battery 16 may be recharged, wirelessly through use of an inductive charger. Accordingly, a receiving circuit (not shown) may be connected to the rechargeable battery for coupling with an external inductive charger which is operatively brought into close proximity to the receiving circuit. Alternatively, power sources such as kinetic energy harvesters (not shown) may also be incorporated into the implantable electronic device 12 in order to recharge the battery 16. The accelerometer 13 is configured to record and/or measure vibration, shock, tilt and rotation amongst others.

Figure 2:
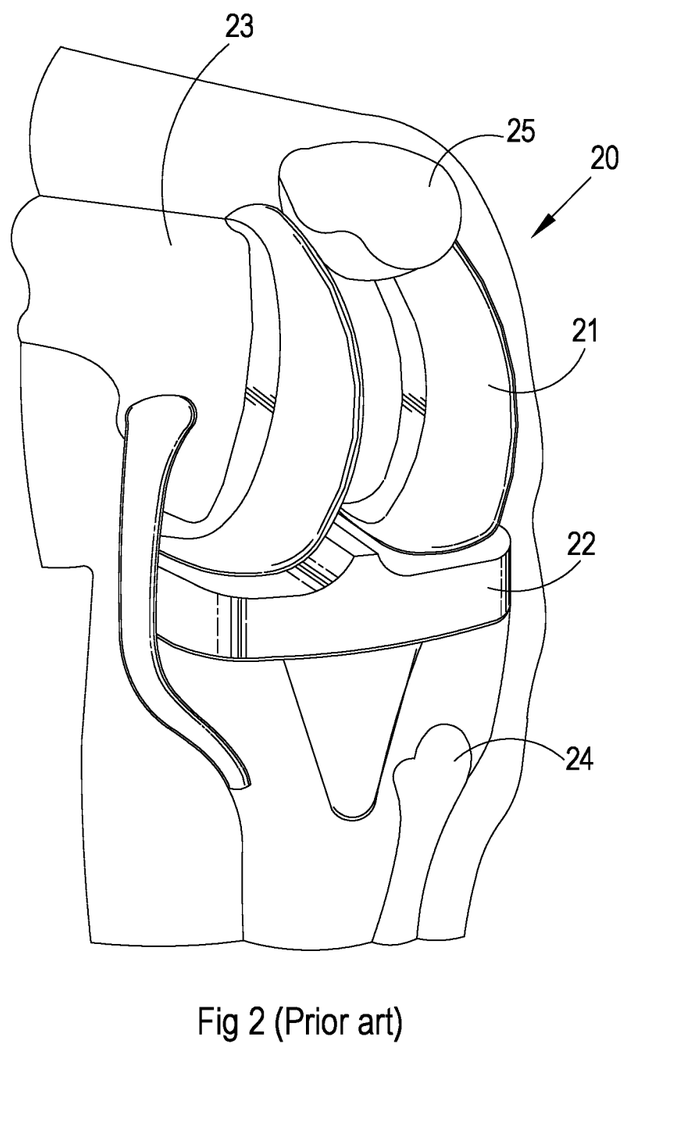
FIG. 2 shows a three-dimensional view of a prior art configuration of a knee prosthesis comprising a femoral component and a tibial component.
Figure 3:
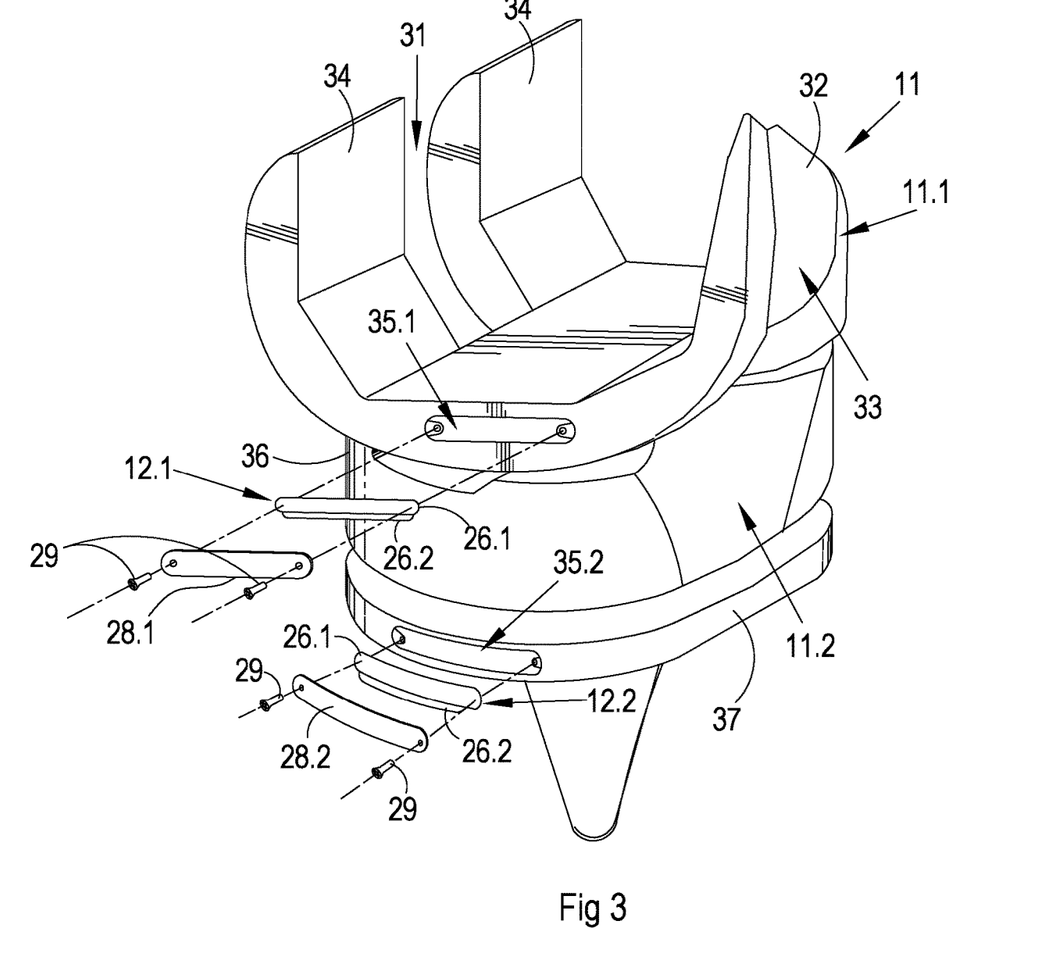
FIG. 3 shows a three-dimensional, partially exploded view of an endoprosthesis in accordance with another aspect of the invention.

With reference to FIG. 2, a conventional, prior art knee prosthesis 20 includes a femoral component 21 which is attached to a degraded distal end of the patient's femur 23 and a tibial component 22 which is connected to a tibia 24 of the patient. The femoral component 21 articulates with the tibial component 22 in order to form an artificial or replacement knee joint. In the event of a total knee replacement, a patellar prosthesis 25 may also be provided. With reference to FIG. 3, the endoprosthesis 11 includes a first part in the form of a femoral component 11.1 and a second part in the form of a tibial component 11.2. The femoral component 11.1 and the tibial component 11.2 articulate to form a knee joint. As illustrated in FIG. 2, the endoprosthesis 11 may also include a patellar prosthesis fitted to a patella, although this has not been illustrated in FIG. 3. The femoral component 11.1 includes a convexly curved, C-shaped head 31. The head 31 has an anterior, pointed protrusion 32 which defines a prominent groove 33 for accommodating and facilitating tracking of the patella. The anterior, pointed protrusion 32 is joined to a pair of posteriorly bifurcating, convexly curved femoral condyles 34. As can be seen in FIG. 3, a laterally inwardly extending blind hole or cavity 35.1, having an oblong cross-section, is provided in a lateral aspect of one femoral condyle 34 of the femoral component 11.1 of the endoprosthesis 11. A first of the two implantable electronic devices 12.1 is operatively removably received or accommodated in the blind cavity 35.1. The blind cavity 35.1 has a length of 15 mm, a breadth of 3.5 mm and a depth of 15 mm. The tibial component 11.2 includes a tibial lining 36 which interfaces with the head 31 of the femoral component 11.1 and a tibial plate 37 which is secured to the tibia 24. A second, laterally inwardly extending blind hole or cavity 35.2 is provided in a lateral aspect of the tibial plate 37 of the tibial component 11.2. This second blind hole 35.2 is configured removably to accommodate the second implantable electronic device 12.2. The second blind hole 35.2 has a length of 15 mm, a breadth of 3.5 mm and a depth of 15 mm, i.e. similar dimensions to the first cavity 35.1. The endoprosthesis activity monitoring system 10 is therefore configured to measure, record and transmit relative acceleration data of the two implantable electronic devices 12.1, 12.2 and, hence, of the femoral component 11.1 and the tibial component 11.2.

Although it has not been illustrated in the Figures, it will be appreciated that additional accelerometers or implantable electronic devices 12 may be provided in or on the patellar prosthesis. Also, multiple accelerometers may be provided on either of, or both of the femoral and tibial components in dedicated cavities or openings. Each implantable electronic device 12 may include multiple accelerometers 13.

Figure 4B:
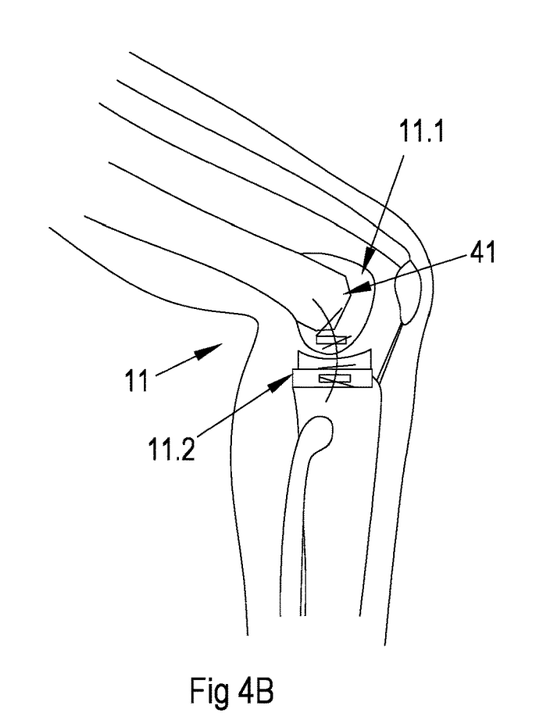

The blind cavities 35.1, 35.2 are provided in lateral aspects of the femoral component 11.1 and tibial component 11.2, respectively, due to the fact that it is an area of the knee that has the least soft tissue cover and is easily accessible. This renders the implantable electronic devices 12.1, 12.2 easily removable, and hence serviceable, for example to replace depleted batteries or malfunctioning components, by way of only minor surgery along any one of the surgical incision lines 40, 41 shown in FIGS. 4A and 4B respectively. In this way, a life span of the implantable electronic devices 12 can be extended without having to remove or interfere with, and potentially compromise, a well-functioning stable knee prosthesis. Furthermore, the accelerometers 13 installed in the endoprosthesis 11 are connected via a wireless digital communication interface to the remote device 18 and are configured to send or transmit accurate information about the type and intensity of activity of the knee to the remote device 18 via a thinnest aspect of the knee across the soft tissue using wireless transmission technology. Furthermore, there would be less tissue signal interference when harvesting data from the implantable electronic device 12 from this location. FIG. 4B illustrates how in an alternative embodiment of the endoprosthesis where the blind cavity is provided in the lateral aspect of the posterolateral condyle, the blind cavity can still be easily accessed with the knee placed in slight flexion.

The endoprosthesis 11 will be made of strong materials that fit the purpose of the implant. The blind cavity 35.1 is provided on the most distal part of the lateral aspect of the lateral femoral condyle 34 (see FIG. 3) which means it is as close as possible to the knee joint. Although this has not been illustrated, each of the pair of femoral condyles 34 of the endoprosthesis 11 may be provided with a blind cavity 35.1 and an associated implantable electronic device 12 removably received therein.

Post-operatively, acceleration and joint rotation data recorded by the accelerometers 13 is collected and stored in memory 15. During a visit to a medical practitioner, the recorded and stored data can be downloaded to the remote device 18, which may be in the form of a smartphone, PDA, watch, wearable device, tablet, laptop, or other computing device, via the wireless communication module 14. The remote device 18 is configured to process the recorded data using suitable algorithms and/or artificial intelligence or machine learning techniques and to display the processed information to the medical practitioner. This may include information of relative acceleration, relative rotation, relative tilt, vibration or force measured across the respective implantable electronic devices 12.1, 12.2. The endoprosthesis activity monitoring system 10 in accordance with the invention provides for more accurate monitoring of the endoprosthesis 11 and permits medical reporting of accurate, in situ, data that will contribute to the health of the patient.

The endoprosthesis activity monitoring system 10 gives a healthcare practitioner an unprecedented level of objective information on physical activity of the limb or replacement body part and gives practitioners the ability to gain easy access to accurate information specific to activity levels of the replacement body part or prosthesis. Furthermore, the activity information analysed and stored can possibly allow for earlier diagnosis of implant specific problems such as loosening of the prosthesis and activity patterns which may lead to a decline in general health of the patient. Other indirect benefits would include motivation of patients with accelerometer-enhanced implants to be more active.

The endoprosthesis activity monitoring system 10 provides for accurate long-term quantification of physical activity in patients following total knee replacement surgery. Using the memory 15 of the implantable electronic devices 12 activity can be recorded over a period of months or longer. Furthermore, permanent or semi-permanent introduction of the accelerometers 13 into the lateral aspects of the endoprosthesis 11 means that the accelerometers 13 can be disposed as close as possible to the knee without causing any discomfort to the user, which consequently results in more accurate measurements. Relative acceleration, rotation, and/or tilt may also be measured by having regard to measurement of the respective implantable electronic devices 12.1, 12.2.

As can best be seen in FIGS. 1 and 3, each implantable electronic device 12 is self-contained and comprises a one-piece, integrated, compact form factor. To this end, each implantable electronic device 12 has a casing 26 which defines an inner cavity for housing components of the implantable electronic device 12. Accordingly, the casing 26 is configured to house the accelerometer 13, memory 15, wireless communication module 14 and battery 16, amongst others, in the inner cavity. Accordingly, each implantable electronic device 12.1, 12.2 is self-contained and, as a whole, is configured to be removably mounted to the respective blind cavities 35.1, 35.2 of the knee prosthesis. The blind cavities 35.1, 35.2 are disposed in areas of the knee which has the least soft tissue cover which renders the implantable electronic devices 12.1, 12.2 easily removable, serviceable and/or replaceable by way of only minor surgery, without unnecessarily compromising structural integrity of the knee prosthesis itself.

The casing 26 includes two complementary, interconnectable parts 26.1, 26.2 which are operatively disconnectably coupled together to form a serviceable pod. The casing 26 may be manufactured from cobalt chrome molybdenum alloy, titanium or titanium alloy or any other material that is compatible with the material properties of the knee prosthesis.

To retain the implantable electronic devices 12.1, 12.2 in their respective blind cavities 35.1, 35.2, each blind cavity 35.1, 35.2 has a complementary cover 28.1, 28.2 which is removably secured over an opening of the blind cavity using either fasteners such as screws 29 which screw into holes or clips (not shown) which retain the cover 28 in position. The Applicant believes that the endoprosthesis 11 has an advantage over other existing activity trackers for prosthetics due to the fact that, despite limited space and the load bearing function of the lateral condyle, provision of the blind cavities 35.1, 35.2 in the lateral aspect of the femoral or tibial condyle, improves accessibility to the self-contained, implantable electronic devices 12 and hence serviceability of these devices.

The invention claimed is:

1. An endoprosthesis which is configured to be fitted to a subject as a replacement body part,
the endoprosthesis having a first part articulating with a second part and a first implantable electronic device removably installed in a blind cavity defined in either one of the first part or second part and wherein the endoprosthesis is a knee prosthesis, the first part being a femoral component and the second part being a tibial component of the knee prosthesis, and
wherein the blind cavity is formed in a lateral aspect of the femoral or tibial component of the knee prosthesis, the blind cavity being configured removably to receive the first implantable electronic device therein and being disposed in an area of a knee which has a least soft tissue cover and accordingly a least signal interference when harvesting data from the first implantable electronic device, thus allowing for easy access to the first implantable electronic device by way of only minor surgery to remove/replace the first implantable electronic device without compromising structural integrity of the knee prosthesis itself.

2. The endoprosthesis as claimed in claim 1,
wherein the blind cavity is formed in the lateral aspect of the femoral component of the knee prosthesis, and
wherein a second blind cavity is formed in a lateral aspect of the tibial component of the knee prosthesis, and
wherein a second implantable electronic device is removably received in the second blind cavity.

3. The endoprosthesis as claimed in claim 2, which includes at least one cover which is configured removably to be secured over one of the blind cavities thus retaining the first or second implantable electronic device in the blind cavity.

4. The endoprosthesis as claimed in claim 1, wherein the blind cavity has dimensions of 20 mm in length, 15 mm in depth, and 3.5 mm in breadth.

5. The endoprosthesis as claimed in claim 1, wherein the blind cavity is formed in the lateral aspect of a femoral condyle.

6. The endoprosthesis as claimed in claim 2, wherein the second blind cavity is formed in the lateral aspect of a tibial condyle.

7. The endoprosthesis as claimed in claim 2, wherein each of the first and second implantable electronic devices includes:
an electromechanical motion sensor which is configured to measure acceleration and rotation of the implantable electronic device;
memory coupled to the electromechanical motion sensor; the memory being configured to store data measured by the electromechanical motion sensor;
a wireless communication transmitter which is communicatively linked to the electromechanical motion sensor and/or memory and is configured to communicate with a remote device; and
a power source configured to power the wireless communication transmitter;
wherein each of the first and second implantable electronic devices is in the form of a self-contained, one-piece, integrated form factor and further includes a casing which defines an inner cavity, the casing being configured to house the electromechanical motion sensor, memory, wireless communication transmitter and power source in the inner cavity such that, the implantable electronic device, as a whole, is configured to be removably mounted to the lateral aspect of the femoral or tibial component of the knee prosthesis in an area of the knee which has the least soft tissue cover which renders the electronic device easily removable, serviceable and/or replaceable by way of only minor surgery without compromising structural integrity of the knee prosthesis.

8. The endoprosthesis as claimed in claim 7, wherein the casing includes two complementary parts which are operatively disconnectably coupled together to form a serviceable pod.

9. The endoprosthesis as claimed in claim 8, wherein the casing is manufactured from cobalt chrome molybdenum alloy, titanium or titanium alloy.

10. The endoprosthesis as claimed in claim 7, wherein the electromechanical motion sensor is a three-axis piezoelectric accelerometer.

11. The endoprosthesis as claimed in claim 10, wherein the power source includes a battery which is configured to power the electromechanical motion sensor and the wireless communication transmitter and wherein the battery is configured to be received in the blind cavity.

12. The endoprosthesis as claimed in claim 7, wherein the power source includes an inductive charger which includes a receiving circuit coupled to the electromechanical motion sensor and the wireless communication transmitter and an inductive charging circuit which is operatively not mounted to the implantable electronic device nor to the knee prosthesis but is configured inductively to power the receiving circuit.

13. The endoprosthesis as claimed in claim 7, which includes a processor which is coupled to the electromechanical motion sensor, memory and the wireless communication transmitter.

* * * * *